United States Patent [19]

Staggs

[11] Patent Number: 4,891,464
[45] Date of Patent: Jan. 2, 1990

[54] CONTROL METHOD FOR OXYGEN ADDITION TO OXIDATIVE REHEAT ZONE OF HYDROCARBON CONVERSION PROCESS

[75] Inventor: Darrell W. Staggs, Hoffman Estates, Ill.

[73] Assignee: UOP, Des Plaines, Ill.

[21] Appl. No.: 930,631

[22] Filed: Nov. 14, 1986

Related U.S. Application Data

[63] Continuation-in-part of Ser. No. 813,432, Dec. 26, 1985, abandoned.

[51] Int. Cl.$^4$ ............................................. C07C 5/333
[52] U.S. Cl. ..................... 585/440; 585/401; 585/441; 585/501; 585/616; 585/633; 585/654; 585/659; 208/DIG. 1; 364/496; 364/500
[58] Field of Search ............... 585/440, 401, 441, 501, 585/616, 633, 654, 659; 364/496, 500; 208/DIG. 1

[56] References Cited

U.S. PATENT DOCUMENTS

| | | | |
|---|---|---|---|
| 3,502,737 | 3/1970 | Ghublikian | 585/440 |
| 3,709,951 | 1/1973 | Hutson, Jr. et al. | 585/440 |
| 3,748,448 | 7/1973 | Sayles et al. | 235/150.1 |
| 3,855,330 | 12/1974 | Mendelsohn et al. | 585/440 |
| 3,904,703 | 9/1975 | Lo et al. | 585/440 |
| 4,069,272 | 1/1978 | Hutson, Jr. | 585/440 |
| 4,132,529 | 1/1979 | Schwimmer | 23/230 A |
| 4,234,410 | 11/1980 | Kelley | 208/57 |
| 4,290,110 | 9/1981 | Makovec | 364/500 |

FOREIGN PATENT DOCUMENTS 197801  1/1978  U.S.S.R. ............................. 585/654

*Primary Examiner*—Asok Pal
*Attorney, Agent, or Firm*—Thomas K. McBride; John F. Spears, Jr.

[57] ABSTRACT

The rate at which an oxygen-containing gas stream is admixed with hydrocarbons and hydrogen upstream of a catalytic hydrogen oxidation zone is controlled on the basis of temperature differentials across the oxidation zone and an upstream catalytic dehydrogenation zone. This control overrides the normal control mode based upon the outlet temperature of the oxidation zone effluent stream, which is the inlet temperature to a subsequent bed of hydrocarbon conversion catalyst. The control method can be used to apply oxidative reheat technology to a variety of processes.

14 Claims, 1 Drawing Sheet

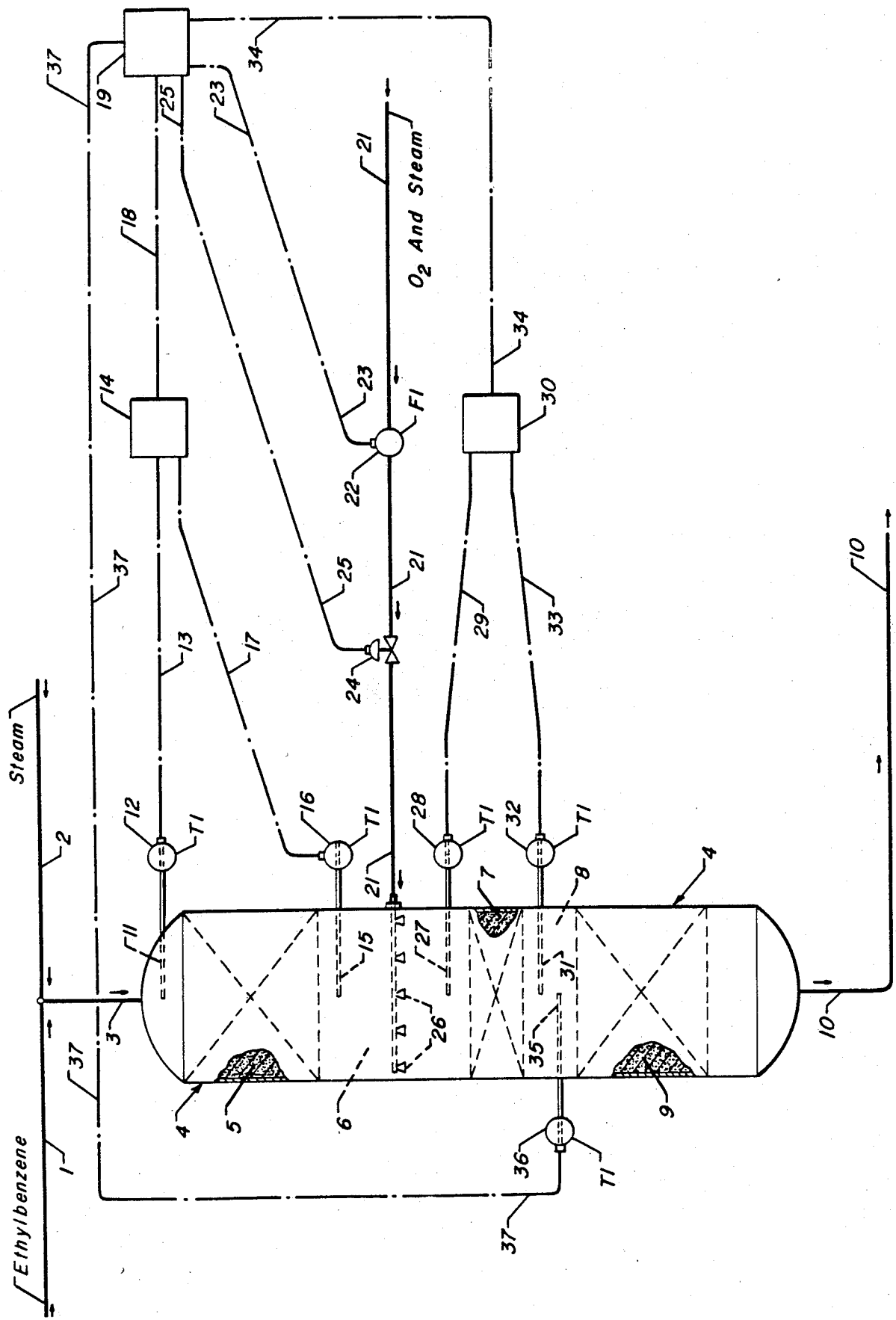

CONTROL METHOD FOR OXYGEN ADDITION TO OXIDATIVE REHEAT ZONE OF HYDROCARBON CONVERSION PROCESS

CROSS REFERENCE TO RELATED APPLICATION

This application is a continuation-in-part of my prior application Ser. No. 813,432 filed on 26 Dec. 1985, now abandoned.

FIELD OF THE INVENTION

The invention relates to the general area of process control as applied to a hydrocarbon conversion process. In particular, the invention relates to a flow control method for use in the catalytic dehydrogenation of an alkylaromatic hydrocarbon. The preferred use of the subject method is in the dehydrogenation of ethylbenzene to styrene. The invention is specifically related to the control of the flow rate of an oxygen-containing gas injected between beds of catalyst in the dehydrogenation process. The invention employs a measurement of the gas flow rate and temperature differentials across both oxidation and dehydrogenation catalyst beds to control gas flow rates.

PRIOR ART

The dehydrogenation of hydrocarbons is well described in the prior art, with both acyclic and aromatic hydrocarbons being thereby converted to the corresponding less saturated products. For instance, dehydrogenation is performed commercially for the production of styrene from ethylbenzene to fulfill the sizable demand for this polymer precursor. U.S. Pat. No. 3,515,766 issued to W. N. Root et al and U.S. Pat. No. 3,409,689 issued to D. J. Ward are pertinent for their showing of typical prior art catalytic steam dehydrogenation processes for alkylaromatics including ethylbenzene. These references describe the admixture of superheated steam into the feed hydrocarbon and the admixture of additional amounts of superheated steam with the reactants between sequential beds of dehydrogenation catalyst to reheat the reactants.

It is also known in the prior art to pass oxygen into a dehydrogenation zone for the purpose of reacting the oxygen with hydrogen released during the dehydrogenation reaction and thereby liberating heat and consuming hydrogen. The processes known to employ this technique utilize a hydrogen oxidation catalyst in an attempt to selectively oxidize the hydrogen rather than feed or product hydrocarbons also present in the dehydrogenation zone. For instance, U.S. Pat. No. 3,437,703 issued to R. E. Reitmeier et al discloses a dehydrogenation process which may utilize either a "homogeneous catalyst system" in which oxidation and dehydrogenation catalysts are admixed or a layered system of individual catalyst beds referred to as a "multi-bed" system. Similarly, U.S. Pat. No. 3,855,330 issued to J. C. Mendelsohn et al discloses a dehydrogenation process using sequential beds of dehydrogenation catalyst and oxidation catalyst. It is taught in this reference that it is desirable that oxygen does not come into contact with the dehydrogenation catalysts, and that the major part or all of the added oxygen is consumed within the bed of oxidation catalyst.

U.S. Pat. No. 3,502,737 issued to J. R. Ghublikian presents a process for the dehydrogenation of ethylbenzene which indicates catalyst activity and stability are maintained by the careful control of the amount of oxygen which is present and by a reduction in the steam which is used in the reaction zone. An oxygen-containing gas such as air is supplied both initially and at interstage points in a carefully controlled manner. It is believed that the teaching of this reference is limited to the use of a catalyst system comprising a physical admixture of the hydrogen oxidation catalyst and the dehydrogenation catalyst, with the presence of oxygen being credited with assisting in the prevention of carbon deposits on the surface of catalytically active sites of the dehydrogenation catalyst.

Those skilled in the art of hydrocarbon conversion or skilled in the art of process control are familiar with a wide number of different control arrangements which can be employed in the operation of a catalytic reactor. It is therefore known to control the operation of a catalytic reactor by controlling the inlet temperature of the feed stream charged to a reactor, by monitoring the temperature of the effluent stream from a reactor, by monitoring both of these temperatures, or by monitoring one or more of these temperatures in conjunction with temperature measurements taken within the reactor itself. The feedstream temperature is normally set at that temperature which will ensure either the initiation of the desired reaction or the accomplishment of a desired amount of reaction in the case of an endothermic reaction. The temperature of the effluent stream or the temperature at various points within the reaction zone is used as a criteria to prevent excessive amounts of reactions from occurring, which in the case of exothermic reactions may lead to damage to the catalyst, the reactor or to degradation of the reactants. Examples of the various modes of temperature control of a reaction zone which may be employed are provided in U.S. Pat. Nos. 4,132,529 issued to M. F. Schwimmer; 4,234,410 issued to C. S. Kelley and 4,290,110 issued to D. J. Makovec. U.S. Pat. No. 3,748,448 issued to J. H. Sayles is pertinent for its showing of a control system for use in the exothermic hydrocracking reaction. The first of these references employs two temperature differential measurements taken across different portions of the reaction zone to control the overall operation of the reaction zone. This process employs two separate catalyst beds, with a quench stream of hydrogen being injected into the reaction zone between the two beds to control the inlet temperature to the second catalyst bed. The rate of flow of the quenched stream is controlled at least in part based upon temperature measurements taken within the reaction zone.

BRIEF SUMMARY OF THE INVENTION

The subject invention provides a method for controlling the rate at which an oxygen-containing gas stream is supplied to a selective hydrogen oxidation zone employed in a hydrocarbon conversion process for the purpose of reheating reactants. The subject control method is effective at quickly sensing and reducing the addition of unneeded quantities of oxygen to the selective hydrogen oxidation zone. This has such advantages as increasing the safety of the overall process and preventing catalyst degradation which may occur due to excess oxygen concentrations being present within the reaction zone. The invention employs the measurement of two temperature differentials. The first temperature differential is measured across an upstream dehydrogenation catalyst bed and is representative of the rate of hydrogen generation upstream of the bed of oxidation catalyst. The second temperature differential is measured across the bed of hydrogen oxidation catalyst and is representative of the oxidation catalyst activity and the degree of conversion occurring in the second bed. A decrease in either temperature differential below preselected minimum values triggers a reduction in the rate of oxygen addition, which is normally controlled on the basis of the temperature of the effluent stream of the oxidation catalyst bed.

One broad embodiment of the subject invention may be characterized as a method of controlling the rate at which an oxygen-containing gas stream is passed into a catalytic oxidative reheating zone of a dehydrogenation process which comprises the steps of measuring a first temperature differential, based on the temperature difference between a first process stream, which comprises a dehydrogenatable hydrocarbon and which enters a first catalyst bed comprising a dehydrogenation catalyst, and a first effluent stream, which comprises hydrogen produced within and emerges from the first catalyst bed; measuring a second temperature differential, based on the temperature difference between a second process stream, which is formed by admixing said oxygen-containing gas stream with said first effluent stream, and which enters a second catalyst bed comprising a selective hydrogen oxidation catalyst, and a second effluent stream, which emerges from the second catalyst bed; measuring the actual rate of flow of said oxygen-containing gas stream; and, adjusting the rate of flow of said oxygen-containing gas stream based upon a maximum allowable rate of flow set by selecting the lower rate of a first allowable maximum rate based upon the first temperature differential and a second allowable maximum rate based upon the second temperature differential.

BRIEF DESCRIPTION OF THE DRAWING

The Drawing is a simplified process flow diagram illustrating the dehydrogenation of ethylbenzene in a reactor employing dehydrogenation catalyst beds 5 and 9 and a selective oxidation catalyst bed 7, with the subject invention controlling the rate of oxygen addition through line 21.

DETAILED DESCRIPTION

Several very useful hydrocarbon conversion processes are very endothermic. These processes often are also hydrogen-producing processes. One example of these processes is the catalytic reforming of naphtha boiling range hydrocarbon mixtures to produce aromatic hydrocarbons or high octane motor fuel as described in the article by M. J. Sterba at page 2 of Volume 15, No. 1 (1976) of "Industrial and Engineering Chemistry—Process Design and Development." Another example of an endothermic hydrogen producing process is the dehydrocyclodimerization of light aliphatic hydrocarbons, preferably propane and butane. An example of this process is described in U.S. Pat. No. 4,548,619 issued to P. C. Steacy. A third example of a hydrogen-producing endothermic process is the dehydrogenation of dehydrogenatable hydrocarbons. As the development of oxidative reheat technology has centered on the dehydrogenation of ethylbenzene, the subject invention will be basically described in a similar context. It could however be applied to these other hydrogen-producing endothermic hydrocarbon conversion processes and for the dehydrogenation of a wide variety of hydrocarbons including $C_2$–$C_{20}$ paraffins.

Processes for the dehydrogenation of aromatic hydrocarbons are in a widespread commercial use. For instance, large quantities of styrene are produced by the dehydrogenation of ethylbenzene. The resultant styrene may be polymerized with itself or it may be copolymerized with butadiene, isoprene, acrylonitrile, etc. Other hydrocarbons which may be dehydrogenated in much the same manner include diethylbenzene, ethyl toluene, propylbenzene, and isopropylbenzene. However, since the great majority of the present commercial dehydrogenation processes are employed by the dehydrogenation of ethylbenzene, the following description of the subject invention will be presented primarily in terms of the dehydrogenation of ethylbenzene. This is not intended to exclude from the scope of the subject invention those other alkylaromatic feed hydrocarbons set out above or those having different ring structures including bicyclic compounds. It is also not intended to exclude from the scope of the invention other common feed hydrocarbons such as $C_2$–$C_{22}$ paraffinic hydrocarbons. Propane, butane and $C_{15}$–$C_{20}$ paraffins are also preferred feeds to the dehydrogenation zone, and the subject control method can be applied to a process for the dehydrogenation of any of these materials with only minor temperature adjustments well within the abilities of those skilled in the art.

The dehydrogenation reaction is highly endothermic. Therefore, passing the reactants through the catalyst bed results in a decrease in the reactants temperature. The endothermicity of the reaction is such that this temperature decrease removes the reactants from the desired temperature range. The reactants are actually cooled to such an extent that the desired reaction does not occur at a commercially feasible rate. The desired or commercially necessary per pass conversion therefore cannot be achieved by simply passing the reactants into contact with a single bed of dehydrogenation catalyst. For this reason, it has become standard commercial practice to in some manner perform interstage reheating. In interstage reheating the reactant effluent of a first bed of dehydrogenation catalyst is heated to the desired inlet temperature of a second downstream bed of dehydrogenation catalyst. This reheating can be performed through direct heat exchange as by the admixture of high temperature steam into the reactant stream emerging from the first catalyst bed. This accomplishes the desired heating, but has a number of drawbacks including the utilities cost of producing the high temperature steam. It also increases the amount of steam which must be condensed to recover the product alkylaromatic hydrocarbons from the effluent stream and increases the total amount of material flowing through the reaction zone, thereby making it more difficult to maintain desired low pressures within the reaction zone.

Another method of interstage reheating comprises the use of indirect heat exchange. In this method the effluent from a dehydrogenation zone is passed through a heat exchanger in which it is heated, and the reactants are then passed into the subsequent dehydrogenation zone. The high temperature fluid employed in this indirect heat exchange method may be high temperature steam, combustion gases, a high temperature process stream or other readily available high temperature fluids. This method of interstage heating does not dilute the reactants but does impose some pressure drop in the system and can expose the reactants to undesirably high temperatures.

A third method of interstage heating is the oxidative reheat method. This is a newer method which it is believed is just now being employed commercially. The driving force for employing the oxidative reheat method is the recognition that the combustion of the hydrogen generated in the dehydrogenation process performs two functions which are beneficial in the dehydrogenation process. First, the consumption of the hydrogen is beneficial in shifting the equilibrium of the dehydrogenation reaction to favor increased amounts of dehydrogenation. Second, the combustion of the hydrogen will release heat sufficient to reheat the reactants to the desired dehydrogenation conditions.

The oxidation is preferably accomplished in the presence of a catalyst which selectively promotes the oxidation of hydrogen as compared to the destructive combustion or oxidation of the more valuable feed and product hydrocarbons. The selective combustion method of interstage reheating presents a more economical dehydrogenation process. It is therefore expected that oxidative reheat will to a significant extent supplant indirect heat exchange as a method of performing the required interstage heating. This trend will also be promoted as more selective catalysts are developed. Therefore, a large number of existing alkylaromatic dehydrogenation process units will be converted from indirect heat exchange to oxidative reheat interstage heating. It is an objective of the subject invention to provide a control method and apparatus for use in oxidative reheat dehydrogenation process units. It is also an objective of the subject invention to provide a method for increasing the safety of operating alkylaromatic dehydrogenation process units. It is another objective of the subject invention to reduce the deleterious action of excess amounts of oxygen on dehydrogenation catalysts employed in the process. This is in recognition of the fact that significant oxygen concentrations can damage or "poison" some commercially employed dehydrogenation catalysts.

In the preferred form of the oxidative reheat process, an oxygen-containing gas stream is admixed with the effluent of a preceding dehydrogenation zone and the resulting admixture is passed into a bed of selective hydrogen oxidation catalyst. To achieve the optimum levels of performance and safety in this process, it is necessary to closely control the rate at which oxygen is passed into the process in this manner. An insufficient amount of oxygen will result in a less than desired consumption of hydrogen and more importantly a less than desired reheating of the reactant stream. The result will be a decrease in the degree of dehydrogenation achieved during passage through the overall reaction zone. It is not normally desired to inject an excess amount of oxygen into any part of the dehydrogenation zone above that required to perform the desired degree of hydrogen combustion. More specifically, in a normal operation no more than 60 mole percent of the net hydrogen produced in the preceding dehydrogenation zone need be combusted to achieve a desired degree of reheating.

The passage of an excess amount of oxygen into the dehydrogenation zone has detrimental effects upon the long term operation of the process. For instance, oxygen will normally serve to deactivate or poison some commercially employed dehydrogenation catalyst. It is therefore undesirable to have residual oxygen emerging from the oxidation catalyst bed and thereupon contacting dehydrogenation catalyst. The effect of this excess oxygen would be a reduction in the activity of the dehydrogenation catalyst which would cause a reduction in the amount of conversion and hydrogen production in the subsequent dehydrogenation zone. If a subsequent stage of oxidative reheat is employed after this second stage of dehydrogenation there would be even less hydrogen to consume in the subsequent oxidation stage. The result would be an even greater excess amount of oxygen contacting downstream dehydrogenation catalyst beds.

Operation of the dehdyrogenation zone in a manner which does not result in the total consumption of the oxygen is also undesirable because of the obvious explosive nature of oxygen-hydrocarbon mixtures. The explosive nature of these mixtures can be essentially negated by properly operating the process to avoid the presence of mixtures being within the explosive range, as through the use of diluents and intentionally low oxygen addition rates. Nevertheless, the safety of the overall process can still be improved by minimizing or totally eliminating the injection of any oxygen which is not consumed within the selective oxidation catalyst bed. This will ensure that an explosive concentration of oxygen does not accumulate within the dehydrogenation zone or the downstream processing equipment. For instance, after condensation of the normally liquid hydrocarbons in the product recovery steps, the concentration of oxygen present in the remaining gas phase would be increased relative to the oxygen concentration in the total dehydrogenation zone effluent stream. This concentration effect could be further increased if a significant amount of hydrogen is consumed within the dehydrogenation zone by selective hydrogen oxidation or if there is only a minor amount of dehydrogenation performed within the dehdyrogenation zone. Lastly, the presence of oxygen is not normally desired in vessels containing hydrocarbons as the oxygen may react with the hydrocarbons to form various undesired oxygenated compounds.

The subject control method eliminates or greatly reduces the possibility of excess amounts of oxygen being added to a dehydrogenation zone. In the normal mode of operation the control method employs the effluent temperature of the relevant bed of oxidation catalyst as a control point for setting the amount of oxygen which is charged into the dehydrogenation zone at a point upstream of the relevant bed of oxidation catalyst. In normal operation if the temperature of the oxidation zone effluent stream decreases the control system calls for an increased amount of oxygen to be passed into the dehydrogenation zone to provide for an increased amount of hydrogen combustion. The increased combustion rate releases additional heat which raises the effluent temperature of the oxidation catalyst bed to the desired set point temperature.

Also, according to the method of the subject invention the temperature differential between the gases entering the bed of oxidation catalyst and the effluent stream of the bed of oxidation catalyst is measured. The measured temperature differential could be compared to a preselected and stored temperature differential. If the measured temperature differential is lower than the desired temperature differential this would be indicative of an undesirably low amount of hydrogen combustion occurring within the oxidation catalyst bed. However, in the subject method the measured differential is converted, as by multiplication by an appropriate conversion factor, into a corresponding rate of flow of the oxygen-containing gas stream which would provide this temperature differential. This rate of flow is employed as a maximum allowable rate of flow for the oxygen-containing gas stream.

The actual rate of flow of the oxygen-containing gas stream is also monitored. This measured rate is then compared to the maximum allowable rate of flow determined on the basis of oxidation catalyst bed temperature differential or to another maximum as set out below. If the actual rate exceeds the maximum allowable set by the temperature differential the actual rate is reduced. This reduction overrides any gas rate called for by the previously described control system, which operates solely on the basis of the temperature of the oxidation catalyst bed effluent stream temperature.

A low amount of hydrogen combustion can be caused by several different factors. First of all, there may be insufficient hydrogen entering the oxidation catalyst bed to support the desired amount of combustion. Another possible defect would be a deactivation of the oxidation catalyst such that it no longer promotes oxidation at an acceptable rate. A third factor which may result in an undesirably low amount of oxidation within the oxidation catalyst bed is an entrance temperature to the oxidation catalyst bed which is below that required to initiate the oxidation reaction. If the temperature differential drops below the desired set point differential for these or other reasons the subject control system overrides the previously determined flow control signal with a signal which decreases the rate of oxygen addition. This may be a total reduction in oxygen flow or a percentage decrease.

The subject control method also monitors the temperature differential across the bed of dehydrogenation catalyst located immediately upstream of the point of addition of the oxygen stream which is controlled by the subject method. This temperature differential is indicative of the rate of dehydrogenation which is occurring within this bed of catalyst. The amount of dehydrogenation which occurs within this catalyst bed is proportional to the temperature differential across the catalyst bed while the absolute temperature of the effluent stream of the catalyst bed is not. A decrease in the temperature differential across this bed will signal that less hydrogen is being produced and therefore there is less hydrogen to be consumed within the subsequent oxidation catalyst bed. A reduced temperature differential will also normally be indicative of a lower requirement for reheating of the effluent of the dehydrogenation catalyst bed. In either instance, the low temperature differential indicates that a lesser amount of oxygen is required to be admixed into the reactants for passage into the oxidation catalyst bed.

In the subject process the temperature differential across the bed of dehydrogenation catalyst bed is used to determine another maximum allowable rate of flow of the oxygen-containing gas stream. This maximum allowable rate is based upon the amount of oxygen required to consume the hydrogen released within the bed of dehydrogenation catalyst. The temperature differential is converted to a maximum allowable flow based upon a knowledge of the heat released during the reaction and the flowrate of the reactants. In the subject method, the actual flow is always controlled to also be below this maximum allowable rate of flow. Therefore, when the temperature differential across the upstream dehydrogenation bed falls the control method signals for a decrease below the normal oxygen supply rate.

The subject method therefore generates two maximum allowable flowrates; one for each temperature differential. The subject method chooses the lower of these two maximum allowable calculated flowrates and reduces the actual rate if the actual rate is in excess of the lower of the two maximum allowable flowrates.

The drawing exemplifies the application of the subject control method to a process for the dehydrogenation of ethylbenzene. In this process, a feed stream comprising relatively high purity ethylbenzene carried by line 1 is admixed with superheated steam from line 2 and passed into the dehydrogenation zone 4 through line 3. The feed admixture enters a bed of dehydrogenation catalyst 5 in which a portion of ethylbenzene is dehydrogenated to produce styrene and hydrogen. The endothermic dehydrogenation reaction results in a reduction in the temperature of the reactant stream as it passes through the dehydrogenation catalyst bed 5. The effluent stream of catalyst bed 5 enters a void cylindrical volume 6 employed for temperature measurement and admixture of the effluent stream with an oxygen-containing gas stream entering the process through line 21. The admixture of the effluent of catalyst bed 5 with the oxygen-containing gas stream is passed into the bed 7 of oxidation catalyst. In this catalyst bed, the hydrogen is selectively combusted to produce steam and to release heat which affects a reheating of the remaining ethylbenzene. The combustion reaction also has the beneficial effect of reducing the hydrogen concentration in the reactant stream. The effluent stream of the catalyst bed 7 emerges into a second cylindrical void volume 8 employed for the purposes of temperature measurement. The reactant mixture of ethylbenzene, steam, styrene and hydrogen then flows into a cylindrical second bed 9 of dehydrogenation catalyst. An additional amount of dehydrogenation is performed within this second bed of dehydrogenation catalyst to effect the production of a dehydrogenation zone effluent stream which is removed from the zone 4 through line 10 and passed into the appropriate styrene recovery facilities as described herein.

The feed stream of ethylbenzene and the steam charged to the process in lines 1 and 2 respectively are heated by means not shown sufficiently to provide an inlet temperature which initiates the dehydrogenation reaction in the first bed of catalyst. After admixture with the oxygen-containing gas stream and passage through the bed of oxidation catalyst, the reactants will have a temperature measured by the temperature measurement means 35 which is equal to the inlet temperature of the second bed of dehydrogenation catalyst. This temperature measurement is converted into a control signal through the temperature indicating and signaling means 36 which transfers a signal through means 37 to the controller 19. The controller 19 will then adjust if necessary the flow rate of the oxygen-containing gas stream passing through line 21 to adjust the temperature of the gases flowing through the cylindrical void volume 8. For instance, if the temperature is below that desired for operation of the dehydrogenation catalyst bed 9, the flowrate of the oxygen-containing gas stream will be increased. Likewise, if the temperature of the effluent stream of the bed of oxidation catalyst is above that desired for the inlet temperature of the second bed of dehydrogenation catalyst the flow rate of the oxidation-containing gas stream will be decreased. This change in the rate of the oxygen-containing gas stream is accomplished by the transmission of a signal through means 25 to the flow control valve 24. This operation is preferably correlated with the measurement of the rate of flow of the oxygen-containing gas stream by the flowrate measurement and indicating means 22 which is also capable of transmitting a signal via means 23 to the controller 19 representative of the instantaneous flow rate of the oxygen-containing gas stream. Means 22 may also contain the apparatus necessary to measure the oxygen concentration of the oxygen-containing gas stream for use in calculating maximum allowable flowrates. The control system operates in this manner unless overridden by a signal based upon one of the two temperature differentials in the subject method.

If for some reason, the dehydrogenation catalyst in bed 5 becomes deactivated or some other factor reduces the amount of dehydrogenation which is effected within the catalyst bed 5 the temperature differential measured across the catalyst bed 5 will decrease. This temperature differential is measured by a first temperature measurement taken by the temperature measuring means 11 and converted to a control signal in the temperature indicating and signal generating means 12. This signal is sent to the comparison means 14 via means 13. The temperature of the effluent of the catalyst bed 5 is monitored through the use of the temperature measurement means 15 and the temperature indicating and signal generation means 16, which transmits a signal through means 17 to the comparator 14. Means 14 generates a signal carried by the signal transmission means 18 to the controller 19. The signal carried by means 18 may be representative of the temperature differential across the catalyst bed 5. It may also carry an alarm signal generated by the excursion of the temperature differential beyond a set point stored within the temperature comparator means 14. Preferably this signal is representative of the maximum allowable gas rate determined by the measured temperature differential across bed 5.

The temperature differential across the bed 7 of oxidation catalyst is measured through the use of the temperature measurement means 27 and the temperature indicating and signal generating means 28 which transmit a signal via means 29 to the temperature comparator 30. This temperature may be different from the temperature of the immediately preceding dehydrogenation zone as measured by means 15 due to admixture with the oxygen-containing gas of line 21. The temperature of the effluent stream of catalyst bed 7 is measured by the temperature measurement means 31 and temperature indicating and signal generation means 32. A signal generated in this manner is transmitted through the signal carrier means 33 to the temperature comparator 30. A signal representative of the temperature differential and possibly other control signals generated by the comparator 30 is then transmitted through means 34 to the control means 19.

The signal(s) transmitted through means 34 is preferably representative of the maximum allowable rate of flow of the oxygen-containing gas stream of line 21. Controller 19 therefore preferably receives signals representative of the two calculated maximum allowable gas flowrates. Controller 19 will act as a low signal selector and employs the lowest of the received signals, including any flowrate signal from signalling means 36, to adjust the actual gas flow rate. In this manner, excessive amounts of oxygen are prevented from entering to downstream catalyst beds 7 or 9 or continuing on and being removed from the dehydrogenation zone in line 10. Other signals may also be transmitted to means 19. For instance, signals representative of one or more of the actual temperatures used in calculating the two temperature differentials or a control signal based upon a temperature or a differential exceeding a present limit could be transmitted to means 19. Other possible variables which may be input to means 19 via signals include the oxygen concentration of the oxygen-containing gas stream or a change in the composition of the hydrocarbon feed stream.

This presentation of one embodiment of the invention has been simplified by not including a description of those pieces of process equipment, such as other control systems, pumps, heat exchangers, etc. which are employed in a process such as this but are not necessary for a description of the operation or construction of the subject invention. This presentation of one embodiment of the invention is not intended to preclude from the scope of the invention those other embodiments set out herein or which are the result of normal and expected modification and variation to those embodiments. For instance, the drawing depicts the use of two separate temperature measurement means 31 and 35. These two separate temperature measurement means both contact gas within the void volume 8 and therefore could be replaced by a single temperature measurement means if so desired. Therefore, temperature measurement means 31 could be employed in the generation of the signal transmitted by means 36 in the embodiment of the drawing. Likewise, extensive variation is possible in both the placement and number of temperature measuring means employed within the process. For instance, the temperature measurement means could be placed immediately adjacent to the external surface of the catalyst beds. Additional temperature sensors can be used within the catalyst beds.

The overall structure of the dehydrogenation zone is also subject to extensive variation in addition to the variations of the control system. For instance, a complex grid of piping having a circular or branching structure could be employed for the distribution of the oxygen-containing gas stream within the void volume 6 instead of the single horizontal conduit having a multiplicity of outlet nozzles 26 as shown in the drawing. It is also possible to place various elements within the void volume 6 for the purpose of admixing the gases emanating from the dehydrogenation zone with the oxygen-containing gas stream. However, the utilization of these mixing devices is not preferred as they tend to increase the cost of the apparatus and may increase the pressure drop through the process which is undesirable. An adequate degree of mixing can be achieved by the proper design and selection of the gas distribution means.

The structure of the overall dehydrogenation zone may also be varied by changing the type of catalyst bed which is employed. For instance, radial flow through annular catalyst beds may be employed instead of the vertical flow through cylindrical catalyst beds depicted in the drawing. It is to be noted that with a radial flow embodiment of the invention the beds of dehydrogenation catalyst and oxidation catalyst may be concentrically located at the same elevation within the vessel. Either the oxidation catalyst or the dehydrogenation catalyst may be located in the outer bed of this arrangement. The gas flow would then pass through cylindrical center pipe regions located in the middle of the radial flow catalyst beds and through annular gas collection and distribution void volumes located between the outer surface of the catalyst beds and the inner wall of the vessel.

Variation is also possible in the number of beds of catalyst which may be employed within the dehydrogenation process. For instance, the dehydrogenation process could employ three separate beds of dehydrogenation catalyst and two beds of oxidation catalyst, or four beds of dehydrogenation catalyst and three beds of oxidation catalyst may be employed. A separate oxygen-containing gas stream would be injected into the gas flow immediately upstream of each bed of oxidation catalyst. The subject control method would then preferably be employed to control the flow rate of each of these gas streams although it is not necessarily to employ the subject method with each bed. With multiple beds of oxidation catalyst the control method would basically just be duplicated for the corresponding number of beds of oxidation catalyst. The temperature differential across each bed of oxidation catalyst and the temperature differential above the immediately preceding bed of dehydrogenation catalyst would be employed.

Those skilled in the art of process control will also recognize that a considerable amount of variation is possible in the equipment employed to practice the subject invention. For instance, both digital and/or analog control elements can be employed in the subject method. The signal transmitting means are preferably wires or similar electrically conductive materials although pneumatic signalling methods using air pressure could be employed if so desired. It is also possible that both types of signal transmitting means may be employed in practicing the invention. The temperature means are preferably thermocouples. Even with thermocouples it is known that a wide variety of different metal pairs could be employed. Furthermore, a single temperature measuring element such as means 11 of the drawing could comprise several thermocouples spaced in different points across the catalyst bed or within the void volume to provide an average temperature or to provide facilities for some type of sophisticated control system designed to eliminate apparently erroneous signals due to the failure of one thermocouple.

It is apparent from the above description of the operation of the subject invention that it would prevent the passage of excessive or unneeded amounts of oxygen into the dehydrogenation zone during periods when control based solely on the effluent temperature of the oxidation zone would not so limit the flow of the oxygen-containing gas stream. This by itself is a significant advantage to the subject invention. The subject invention therefore increases both the safety of the process and the longevity of the dehydrogenation catalyst. An additional advantage of the subject process is that it is responsive to conditions measured upstream of the point of addition of the oxygen. Therefore, it will respond to changed conditions sooner than a control method which is dependent upon signals generated downstream of the point of oxygen addition or downstream of the bed of oxidation catalyst.

The total amount of dehydrogenation catalyst employed in the process may be divided into ten or more separate beds, but the dehydrogenation zone preferably comprises two or three catalyst beds with means for the intermediate addition and admixture of any added steam and the oxygen supply steams. Suitable systems for this may be patterned after those presented in U.S. Pat. Nos. 3,498,755; 3,515,763; and 3,751,232. The catalyst beds may be contained in separate reaction vessels or they may be enclosed within a larger overall vessel or structure. The use of radial flow annular catalyst beds in a stacked configuration in a single overall vessel is sometimes preferred although the invention can be used with vertical flow in cylindrical beds as shown in the drawing.

Dehydrogenation catalysts generally consist of one or more metallic components selected from Groups VI and VIII of the Periodic Table. One typical catalyst for the dehydrogenation of alkylaromatics comprises 85% by weight ferric oxide, 2% chromia, 12% potassium hydroxide and 1% sodium hydroxide. A second dehydrogenation catalyst, which is used commercially, consists of 87-90% ferric oxide, 2-3% chromium oxide and from 8-10% potassium oxide. A third typical catalyst comprises 90% by weight iron oxide, 4% chromia and 6% potassium carbonate. Methods for preparing suitable catalysts are well known in the art. This is demonstrated by the teachings of U.S. Pat. No. 3,387,053, which describes the manufacture of a catalytic composite of at least 35 wt. % iron oxide as an active catalytic agent, from about 1-8 wt. % zinc or copper oxide, about 0.5-50 wt. % of an alkali promoter, and from about 1-5 wt. % chromic oxide as a stabilizer and a binding agent. U.S. Pat. No. 4,467,046 also describes a catalyst for the dehydrogenation of ethylbenzene in the presence of steam. This catalyst contains 15 to 30 wt. % potassium oxide, 2 to 8% cerium oxide, 1.5 to 6% molybdenum oxide, 1 to 4% calcium carbonate with the balance iron oxide.

Dehydrogenation conditions in general include a temperature of about 538 degrees to 750 degrees C. (1000 degrees-1382 degrees F.) and preferably about 565 degrees to about 675 degrees C. (1050 degrees F.). The temperature required for efficient operation of any specific dehydrogenation process will depend on the feed hydrocarbon and the activity of the catalyst employed. The pressure maintained within the dehydrogenation zone may range from about 100 to about 750 mm Hg, with a preferred range of pressures being from 250 to 700 mm Hg. The operating pressure within the dehydrogenation zone is measured at the inlet, midsection, and outlet of the zone to thereby provide an approximately average pressure. The combined feed stream is charged to the dehydrogenation zone at a liquid hourly space velocity, based on liquid hydrocarbon charge at 60 degrees F. (15.6 degrees C.), of about 0.1 to about 2.0 $hr^{-1}$, and preferably from 0.2 to 1.0 $hr^{-1}$. Further information on the operation of a reaction zone and catalysts for the dehydrogenation of ethylbenzene can be obtained by reference to U.S. Pat. No. 4,551,571.

The desired inlet temperature to any particular bed of dehydrogenation catalyst, and the desired temperature differential across each bed, will be dependent on several factors. The most important of these is the identity of the feed. For instance, the desired inlet temperature for the dehydrogenation of ethylbenzene is approximately 648 degrees C. (1200 degrees F.). The desired inlet temperature for the dehydrogenation of isobutane is about 625 degrees C. (1157 degrees F.) and is about 690 degrees C. (1274 degrees F.) for the dehydrogenation of ethane. The desired temperature differential across a bed of dehydrogenation catalyst used in the dehydrogenation of ethylbenzene is about 30–50 Celsius degrees (48–80 Fahrenheit degrees). The differential across a bed of dehydrogenation catalyst employed in dehydrogenation of isobutane is about 60 Celsius degrees (96 Fahrenheit degrees). The preferred differential will depend upon such factors as the number of beds of dehydrogenation catalyst employed in the reaction zone, the selectivity of the catalyst and the placement of the bed in the series of dehydrogenation catalyst beds. For instance, in a system employing three beds of dehydrogenation catalyst the temperature differential across the beds will be different due to a different preferred outlet temperature for each bed coupled with a constant inlet temperature. The differentials for the first to third beds would be 70, 53 and 41 Celsius degrees, respectively. For a five-bed system, the preferred differentials would be adjusted to account for a reduced preferred inlet temperature of 610 degrees C. (1130 degrees F.). The previously cited patent to Mendelsohn et al presents a table of temperatures at the inlets and outlets of both the dehydrogenation and oxidation catalyst beds in a process for the dehydrogenation of ethylbenzene.

Those skilled in the art have a pre-existing body of knowledge as to an expected temperature differential across any specific bed of dehydrogenation catalyst in which the hydrocarbon conversion process step of the subject invention is performed. Alternatively, this temperature differential can be calculated based upon a knowledge of the reactant flowrate through the reactor, the expected degree of conversion, and the heat of the reaction of the desired dehydrogenation reaction. This therefore is a straightforward calculation based upon easily determinable factors. The factors however are unique to each application of the claimed method and therefore may result in different values being obtained in different situations.

The desired temperature differential across a stage or bed of oxidation catalyst in which hydrogen is selectively reacted with oxygen can be determined from a subtraction between two different temperatures. This is the desired outlet temperature for the effluent of the bed of oxidation catalyst (which is the desired inlet temperature of the downstream bed of hydrocarbon conversion catalyst) minus the inlet temperature to the bed of oxidation catalyst (which will normally be essentially the same as the effluent temperature of the preceding bed of hydrocarbon conversion catalyst).

The normal rate of flow of the oxygen-containing gas stream may also be easily determined on the basis of a simple calculation within the capability of one of ordinary skill in the art. The rate of flow of the oxygen-containing gas stream is dependent upon the amount of oxygen required to release the desired amount of heat by the selective oxidation of hydrogen. One of ordinary skill in the art may readily compute the amount of oxygen required to reheat the reactants based on the heat of reaction of this reaction, the rate of flow of the reactants and their heat capacities. It is also a simple and direct procedure to automate these calculations if it is so desired to have them be performed by the logic elements of the control apparatus employed in the method.

When an alkylaromatic hydrocarbon is to be dehydrogenated, it is preferably admixed with superheated steam to counteract the temperature lowering effect of the endothermic dehydrogenation reaction. The presence of steam has also been described as benefiting the stability of the dehydrogenation catalyst by preventing the accumulation of carbon deposits. Preferably, the steam is admixed with the other components of the feed stream at a rate of about 0.8 to about 1.7 pound of steam per pound of feed hydrocarbon. Other quantities of steam may be added after one or more subsequent beds if desired. However, the dehydrogenation zone effluent stream should contain less than about 3 pounds of steam per pound of product hydrocarbon and preferably less than 2 pounds of steam per pound of product hydrocarbon. It is preferred not to admix steam with paraffinic feed hydrocarbons.

The effluent stream removed from the overall dehydrogenation zone is normally heat exchanged for the purpose of lowering its temperature and for the recovery of heat. The effluent stream may be heat exchanged against a stream of steam, a reactant stream of this or another process or used as a heat source for fractionation, etc. Commercially, the effluent stream is often passed through several heat exchangers thereby heating a number of different streams. This heat exchange should cool the dehydrogenation zone effluent stream sufficiently to cause the condensation of at least 95 mole percent of any feed and product $C_6$-plus hydrocarbons and also at least 95 mole percent of the water vapor present in the reactor effluent. The use of a quench zone to accomplish this condensation is not preferred. Essentially all of the styrene or other product hydrocarbon, most water and other readily condensible compounds present in the effluent stream are thereby converted to liquids. This produces a mixed phase stream which is passed into a phase separation vessel. This procedure allows a facile crude separation by decantation of the hydrocarbons from the water and hydrogen present in the effluent stream. The styrene present in the dehydrogenation zone effluent stream becomes part of a hydrocarbon stream which is withdrawn from the separation vessel and transferred to the proper separation facilities.

Preferably, the styrene or other product hydrocarbon is recovered from the hydrocarbon stream by using one of the several fractionation systems known in the art. This fractionation will preferably yield a relatively pure stream of ethylbenzene, which is recycled, and an additional stream comprising benzene and toluene. These two aromatic hydrocarbons are by-products of the dehydrogenation reaction. They may be recycled in part as taught in U.S. Pat. No. 3,409,689 and British Pat. No. 1,238,602 or entirely rejected from the process. Styrene is recovered as a third stream, which is withdrawn from the process. If desired, methods other than fractionation may be used to recover the styrene. For instance, U.S. Pat. No. 3,784,620 teaches the separation of styrene and ethylbenzene through the use of a polyamide permeation membrane such as nylon-6 and nylon 6,10. U.S. Pat. No. 3,513,213 teaches a separatory method employing liquid-liquid extraction in which anhydrous silver fluoroborate is used as the solvent. Similar separatory methods utilizing cuprous fluoroborates and cuprous fluorophosphates are described in U.S. Pat. Nos. 3,517,079; 3,517,080; and 3,517,081.

The recovery of styrene through the use of fractionation is described in several references including U.S. Pat. No. 3,525,776. In this reference, the hydrocarbonaceous phase removed from the phase separation zone is passed into a first column referred to as a benzenetoluene column. This column is operated at a subatmospheric pressure to allow its operation at lower temperatures and hence reduce the rate of styrene polymerization. Various inhibitors such as elemental sulfur, 2,4- dinitrophenol or a mixture of N-nitroso diphenylamine and a dinitroso-o-cresol may be injected into the column for this same purpose. Sulfur can also be introduced into this column by returning at least a portion of the high molecular weight material separated from the bottoms stream of a styrene purification column. A more detailed description of this is contained in U S. Pat. Nos. 3,476,656; 3,408,263; and 3,398,063. There is effected within the benzene-toluene column a separation of benzene and toluene from the effluent to produce an overhead stream which is substantially free of styrene and ethylbenzene. This stream preferably contains at least 95 mole percent benzene and toluene. The bottoms of the benzene-toluene column is passed into a second fractionation column from which ethylbenzene is removed as an overhead product and recycled. The bottoms stream of this column is then purified to obtain the styrene. Product recovery techniques directed to the recovery of vinyltoluene via fractionation and the use of chemical additives to inhibit polymerization are described in U.S. Patent Nos. 4,417,085 and 4,492,675. The use of inhibitors and alternative fractionation techniques for readily polymerizable vinyl aromatic compounds is also described in U.S. Pat. No. 4,469,558.

The oxygen consumed during the hydrogen combustion is preferably admixed into the reactant stream at the point of interstage heating as part of an oxygen supply stream. The oxygen supply stream may be air but is preferably a gas having a lower oxygen content than air. This is preferred since the dilution of the oxygen reduces the risk of an explosion. Dilution with steam is preferred. Pure oxygen or oxygen enriched air could be employed if the risk of an explosion can be eliminated. In that instance, the preferred oxygen concentration in the oxygen supply stream would be primarily a matter of economics and would be determined by a comparison of the advantage of having pure oxygen to the cost of obtaining the oxygen. The basic disadvantages of the presence of nitrogen as a diluent are the dilution of the hydrogen-containing gas stream removed from the product separation vessel and the fact that the nitrogen passes through the dehydrogenation zone thereby increasing the pressure drop through the catalyst bed and the absolute pressure being maintained within the dehydrogenation zone. On the other hand, the presence of nitrogen favorably affects the equilibrium conversion level by acting as a diluent.

The oxidation catalyst employed in the subject process to promote the interstage hydrogen oxidation may be any commercially suitable catalyst which meets the required standards for stability and activity and which possesses high selectivity for the oxidation of hydrogen as compared with the oxidation of the feed or product hydrocarbon. That is, the oxidation catalyst must have a high selectivity for the oxidation of hydrogen with only small amounts of the feed or product hydrocarbon being oxidized. The oxidation catalyst will have a different composition than the dehydrogenation catalyst. The preferred oxidation catalyst comprises a Group VIII noble metal and a metal or metal cation which possesses a crystal ionic radius greater than 1.35 angstroms, with both of these materials being present in small amounts on a refractory solid support. The preferred Group VIII metals are platinum and palladium, but the use of ruthenium, rhodium, osmium and iridium is also contemplated. The Group VIII metal is preferably present in an amount equal to 0.01 to 5.0 wt. % of the finished catalyst. The metal or metal cation having a radius greater than 1.35 angstroms is preferably chosen from Groups IA or IIA and is present in an amount equal to about 0.01 to about 20 wt. % of the finished catalyst. This component of the catalyst is preferably barium, but the use of other metals including rubidium or cesium is also contemplated. A preferred catalyst is described in U.S. Pat. Nos. 4,418,237 and 4,435,607. Further information on the composition, method of manufacture and use of a particularly preferred oxidation catalyst is available in U.S. Pat. No. 4,565,898, which is incorporated herein by reference.

The preferred solid support is alumina having a surface area between 1 and 300 $m^2/g$, an apparent bulk density of between about 0.2 and 1.5 g/cc, and an average pore size greater than 20 angstroms. The metal-containing components are preferably impregnated into solid particles of the solid support by immersion in an aqueous solution followed by drying and calcination at a temperature of from about 500 degrees to 600 degrees C. in air. The support may be in the form of spheres, pellets or extrudates. The total amount of oxidation catalyst present within the dehydrogenation zone is preferably less than 30 wt. % of the total amount of dehydrogenation catalyst and more preferably is between 5 and 15 wt. % of this total amount of dehydrogenation catalyst.

The conditions utilized during the contacting of the reactant streams with the different beds of oxidation catalyst will be set to a large extent by the previously referred to dehydrogenation conditions. The preferred outlet temperature of any bed of oxidation catalyst is the preferred inlet of the immediately downstream bed of dehydrogenation catalyst. The temperature rise across any bed of oxidation catalyst is preferably less than 100 Celsius degrees. The liquid hourly space velocity, based on the liquid hydrocarbon charge at 60 degrees F., is preferably between 2 and 10 $hr^{-1}$. It is preferred that substantially all of the oxygen which enters a bed of oxidation catalyst is consumed within that bed of oxidation catalyst and that the effluent stream of any bed of oxidation catalyst contains less than 0.1 mole percent oxygen. The total moles of oxygen charged to the dehydrogenation zone is preferably less than 30% of the total moles of hydrogen available within the dehydrogenation zone for combustion and is therefore dependent on the conversion achieved in the dehydrogenation zone and the amount of hydrogen lost in solution or in any off-gas streams. This available hydrogen is the sum of any hydrogen recycled to the dehydrogenation zone and the hydrogen produced in all but the last bed of dehydrogenation catalyst. As used herein, the term "substantially all" is intended to indicate a major fraction of the indicated chemical compound(s) which have been acted upon in the manner described, with this major fraction preferably being over 90 mole percent and more preferably over 95 mole percent. As previously mentioned, the subject process is not limited to the production of styrene and may be used to produce paramethylstyrene by dehydrogenation of ethyltoluene or for the production of other unsaturated product hydrocarbons such as ethylene, propylene, one or more butylenes or $C_{10}$–$C_{15}$ acyclic olefins.

I claim as my invention:

1. A method of controlling the rate at which an oxygen-containing gas stream is passed into a catalytic oxidative reheating zone of an endothermic hydrogen-producing hydrocarbon conversion process which comprises the steps of:

(a) measuring a first temperature differential based on the temperature difference between a first process stream, which comprises a feed hydrocarbon and which enters a first catalyst bed comprising a hydrocarbon conversion catalyst, and a first effluent stream, which comprises hydrogen produced within and emerges from the first catalyst bed;

(b) measuring a second temperature differential, based on the temperature difference between a second process stream, which is formed by admixing said oxygen-containing gas stream with said first effluent stream, and which enters a second catalyst bed comprising a selective hydrogen oxidation catalyst and a second effluent stream, which emerges from the second catalyst bed;

(c) measuring the actual rate of flow of said oxygen-containing gas stream; and, (d) adjusting the rate of flow of said oxygen-containing gas stream based upon a maximum allowable rate of flow set by selecting the lower rate of a first allowable maximum rate based upon the first temperature differential and a second allowable maximum rate based upon the second temperature differential.

2. The method of claim 1 further characterized in that the temperature of the second effluent stream is also measured and the rate of flow of the oxygen-containing gas stream is controlled on the basis of the temperature of the second effluent stream if the actual rate of flow of the oxygen-containing gas stream is less than the first allowable maximum rate or the second allowable maximum rate.

3. The method of claim 2 further characterized in that the set point for the temperature of the second effluent stream is the desired inlet temperature of a downstream third catalyst bed comprising a dehydrogenation catalyst.

4. The method of claim 1 further characterized in that the rate of flow of said oxygen-containing gas stream is decreased if the first or the second temperature differential decreases to below 40 degrees Celsius.

5. The method of claim 1 further characterized in that the temperature differentials are based upon temperature measurements performed at points located outside of the first and the second catalyst beds.

6. The method of claim 1 further characterized in that the first process stream comprises an alkylaromatic feed hydrocarbon.

7. The method of claim 6 further characterized in that the feed hydrocarbon is ethylbenzene.

8. The method of claim 1 further characterized in that the first process stream comprises a $C_2$–$C_{22}$ paraffinic feed hydrocarbon.

9. The method of claim 1 further characterized in that the oxygen-containing gas stream comprises air.

10. The method of claim 1 further characterized in that the endothermic hydrocarbon conversion process comprises the dehydrogenation of the feed hydrocarbon.

11. A method of controlling the rate at which an oxygen-containing gas stream is passed into a catalytic oxidative reheating zone of a dehydrogenation process which comprises the steps of:

(a) measuring a first temperature differential based on the temperature difference between a first process stream, which comprises a dehydrogenatable hydrocarbon and which enters a first catalyst bed comprising a dehydrogenation catalyst, and a first effluent stream, which comprises hydrogen produced within and emerges from the first catalyst bed;

(b) measuring a second temperature differential, based on the temperature difference between a second process stream, which is formed by admixing said oxygen-containing gas stream with said first effluent stream, and which enters a second catalyst bed comprising a selective hydrogen oxidation catalyst and a second effluent stream, which emerges from the second catalyst bed;

(c) measuring the temperature of said second effluent stream, and adjusting the flowrate of said oxygen-containing gas stream on the basis of the temperature of said second effluent stream;

(d) measuring the actual rate of flow of said oxygen containing gas stream; and, (e) reducing the rate of flow of said oxygen-containing gas stream if it exceeds a maximum allowable rate of flow set by selecting the lower rate of a first allowable maximum rate based upon the first temperature differential and a second allowable maximum rate based upon the second temperature differential.

12. The method of claim 11 further characterized in that the dehydrogenatable hydrocarbon is ethylbenzene.

13. The method of claim 11 further characterized in that the dehydrogenatable hydrocarbon is an acyclic hydrocarbon.

14. The method of claim 13 further characterized in that the dehydrogenatable hydrocarbon is a $C_2$–$C_{22}$ paraffinic hydrocarbon.

* * * * *